US00PP31106P2

(12) United States Plant Patent
Zlesak

(10) Patent No.: US PP31,106 P2
(45) Date of Patent: Nov. 26, 2019

(54) POLYANTHA ROSE PLANT NAMED 'ZLEPOLTWO'

(50) Latin Name: *Rosa hybrida*
Varietal Denomination: Zlepoltwo

(71) Applicant: The Conard-Pyle Company, West Grove, PA (US)

(72) Inventor: David Charles Zlesak, River Falls, WI (US)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 16/350,689

(22) Filed: Dec. 20, 2018

(51) Int. Cl.
*A01H 5/02* (2018.01)
*A01H 6/74* (2018.01)

(52) U.S. Cl.
USPC ..... Plt./144

(58) Field of Classification Search
USPC ..... Plt./144
CPC ..... A01H 5/02; A01H 6/74
See application file for complete search history.

*Primary Examiner* — Annette H Para
(74) *Attorney, Agent, or Firm* — Buchanan Ingersoll & Rooney PC

(57) ABSTRACT

A new and distinct variety of polyantha rose plant, herein referred to as 'Zlepoltwo', is provided which forms abundantly on a substantially continuous basis attractive, double white colored blossoms. Attractive, semi-glossy, medium green foliage is formed, which contrasts beautifully with the blossoms. The vegetation is vigorous and the growth habit is very bushy and compact. The new variety is well suited for providing attractive ornamentation in the landscape.

1 Drawing Sheet

Botanical/commercial classification:
Latin name—*Rosa hybrida.*
Common name—Polyantha Rose Plant.
Varietal denomination: 'Zlepoltwo'.

SUMMARY OF THE INVENTION

The new variety of *Rosa hybrida* polyantha rose plant was created during June of 1998 at Rhinelander, Wis., U.S.A., by open pollination. The female parent (i.e., the seed parent) was an unnamed seedling (non-patented). The male parent was from a mix of unnamed seedlings (none patented).

The parentage of the new variety can be summarized as follows:

unnamed seedling x unnamed seedling

The seeds resulting from the above pollination were sown and small plants were obtained which were physically and biologically different from each other. Selective study resulted in the identification of a single plant of the new variety.

It was found that the new variety of polyantha rose plant of the present invention possesses the following combination of characteristics:

(a) forms attractive, double white colored blossoms abundantly and substantially continuously,
(b) exhibits a very bushy and compact growth habit,
(c) forms vigorous vegetation,
(d) provides attractive ornamental semi-glossy, medium green foliage, and
(e) exhibits excellent disease resistance.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the unnamed female parent (i.e., the seed parent) displays less vigorous vegetation, lighter green foliage, semi-double pink blooms, and exhibits less flowers compared to the new variety. Moreover, the new variety can be readily distinguished from related similar non-parental varieties. For example, 'White Pet' (non-patented) displays larger bloom size and darker green foliage compared to the new variety.

The new variety has been found to undergo asexual propagation in Cochranville, Pa. by a number of routes, including softwood and semi-hardwood cuttings. Asexual propagation by stem cuttings in Cochranville, Pa. has shown that the characteristics of the new variety are stable and are strictly transmissible by such asexual propagation from one clonal generation to another. Accordingly, the new variety undergoes asexual propagation in a true-to-type manner.

The new variety has been named 'Zlepoltwo'.

BRIEF DESCRIPTION OF THE PHOTOGRAPH

The accompanying photograph of FIG. 1 shows as nearly true as it is reasonably possible to make the same, in a color illustration of this character, a typical specimen of the new variety. The rose plant of the new variety illustrated herein was approximately three years of age and was observed during May of 2018 while growing on its own roots and growing outdoors at Cochranville, Pa., U.S.A.

FIG. 1—illustrates a specimen the plant with blossoms at varying stages of opening.

DETAILED BOTANICAL DESCRIPTION

The chart used in the identification of the colors is that of The Royal Horticultural Society (R.H.S. Colour Chart, 2015 edition), London, England. The terminology which precedes reference to the chart has been added to indicate the corresponding color in more common terms. The description is based on the observation of three-year-old specimens of the new variety during May while growing on their own roots and growing in containers at Cochranville, Pa., U.S.A.

Class: Polyantha Rose Plant.

Plant:

*Habit*.—Very busy and compact.

*Height*.—Approximately 40.0 cm on average in a three-gallon container.

*Width*.—Approximately 40.0 cm on average in a three-gallon container.

Branches:

*Color*.—Young stems: commonly near Yellow-Green Group 144A. — old wood: commonly near Green Group 137B.

*Length*.—Main stems: approximately 25.0 cm on average. — secondary stems: approximately 9.0 cm on average.

*Prickles*.—Young prickles: length is approximately 2.0 mm on average, width is approximately 1.0 mm at point of attachment, quantity is very sparse, and color is commonly near Greyed-Orange Group 173D. — old prickles: length is approximately 4.0 mm on average, width is approximately 2.0 mm on average, quantity is very sparse, and color is commonly near Greyed-Orange Group 173D.

Foliage:

*General appearance*.—Medium green with a semi-glossy aspect.

*Number of leaflets*.—3, 5, and 7.

*5-leaflet leaf length*.—Approximately 6.0 cm on average. — width: approximately 4.0 cm on average.

*Young foliage*.—Upper surface color: commonly near Yellow-Green Group 144A. — under surface color: commonly near Yellow-Green Group 144B.

*Old foliage*.—Upper surface color: commonly near Green Group NN137A. — under surface color: commonly near Green Group NN137D.

Leaflets:

*Shape*.—Ovate.

*Texture*.—Upper and under surface is smooth.

*Terminal leaflet*.—Length: approximately 2.5 cm on average. — width: approximately 1.8 cm on average.

*Lower leaflet*.—Length: approximately 1.5 cm on average. — width: approximately 1.0 cm on average.

*Leaf margin*.—Serrate.

*Petiole*.—Upper surface: color is commonly near Yellow-Green Group 144A and texture is sparsely glandular and moderately pubescent. — under surface: color is commonly near Yellow-Green Group 144A and texture is sparsely glandular and moderately pubescent, older leaflets have small prickles less than 1.0 mm in length.

*Rachis*.—Color of upper and under surfaces: commonly near Yellow-Green Group 144A.

*Stipules*.—Margin: entire to erose. — length: approximately 10.0 mm on average. — width: approximately 3.0 mm on average. — color of upper and under surfaces: commonly near Green Group 143B.

Inflorescence:

*Number of flowers*.—Generally about 50-60 blooms on average on a plant at once.

*Number of blooms per stem or in a cluster*.—Generally up to 10 blooms per cluster.

*Bud*.—Shape: round. — length: approximately 6.0 mm on average. — width: approximately 6.0 mm on average. — color when opening: commonly between near Yellow-Green Group 145D and Green-White Group 157D.

*Sepals*.—Number: commonly 5 on average. — length: approximately 7.0 mm on average. — width: approximately near 3.0 mm on average. — margin: entire with extensions on two or three sepals measuring approximately 3.0 mm in length on average and 1.0 mm in width on average. — upper surface color and texture: commonly near Green Group 138B; covered in short pubescence. — under surface color and texture: commonly near Yellow-Green Group 144A; puberulent.

*Receptacle*.—Pistils stand on the bottom and wall. — color: commonly near Yellow-Green Group 144A. — diameter: approximately 3.0 mm on average. — surface texture: smooth. — shape: round.

*Peduncle*.—Length: approximately 1.5 cm on average. — diameter: approximately 1.0 mm on average. — surface texture: smooth. — color: commonly near Yellow-Green Group 144A.

*Flower*.—Diameter: approximately 2.8 cm on average. — height: approximately 1.3 cm on average. — duration: flower is on the plant approximately 5 days. — form: double. — number of petals under normal conditions: approximately 25 petals on average. — shape of the petal: — overall: broadly obovate. — base: cuneate. — apex rounded. — petal length: approximately 8.0 mm on average. — petal width: approximately 6.0 mm on average. — petal margin: entire. — petal drop: good. — fragrance: slight and sweet. — color when opening begins: Upper petal surface: commonly near Yellow Group 4D with a hint of near Yellow Group 4C at the point of attachment. Under petal surface: commonly near Yellow Group 4D. — color at end of blooming: Upper petal surface: commonly near White Group NN155B. Under petal surface: commonly near White Group NN155B.

*Petaloids*.—Number: approximately 3 per flower on average. — color: upper and under surfaces are commonly near Yellow Group 4D. — length: approximately 6.0 mm on average. — width: approximately 3.0 mm on average. — texture: smooth. — margins: variable, entire to erose. — shape: variable, oblong and mostly curving inward; apex is round; base is cuneate.

*Stamen*.—Number: is approximately 50 on average. — anthers: coloration is commonly near Yellow Group 9A. — filaments: length is approximately 1.0 mm on average and coloration is commonly near Yellow Group 9B.

*Pistils*.—Arrangement is separate and free; number is approximately 6 on average. — styles: length is approximately 2.0 mm on average and coloration is commonly near Greyed-Green Group 193B. — stigmas: diameter is approximately 1.0 mm on average and coloration is commonly near Greyed-Green Group 193A.

*Pollen*.—Color is commonly near Yellow-Orange Group 21A and a moderate amount is present.

*Hips/seeds*.—None observed.

Development:

*Vegetation*.—Medium green, semi-glossy, vigorous and strong.

*Blooming*.—Abundant and substantially continuous from spring through frost.

*Resistance to disease*.—Excellent resistance to black spot, rust, and powdery mildew.

Cytology:

*Ploidy*.—Diploid (2n=2x=14); meristematic root tip cells in the stage of metaphase of mitosis were observed to have 14 chromosomes under a light microscope at 400× magnification.

'Zlepoltwo' has not been observed under all possible environmental conditions to date. Accordingly, it is possible that the phenotypic expression may vary somewhat with changes in light intensity and duration, cultural practices, and other environmental conditions.

I claim:

1. A new and distinct variety of Polyantha Rose plant characterized by the following combination of characteristics:

(a) forms attractive, double white colored blossoms abundantly and substantially continuously, (b) exhibits a very bushy and compact growth habit, (c) forms vigorous vegetation, (d) provides attractive ornamental semi-glossy, medium green foliage, and (e) exhibits excellent disease resistance;

substantially as herein shown and described.

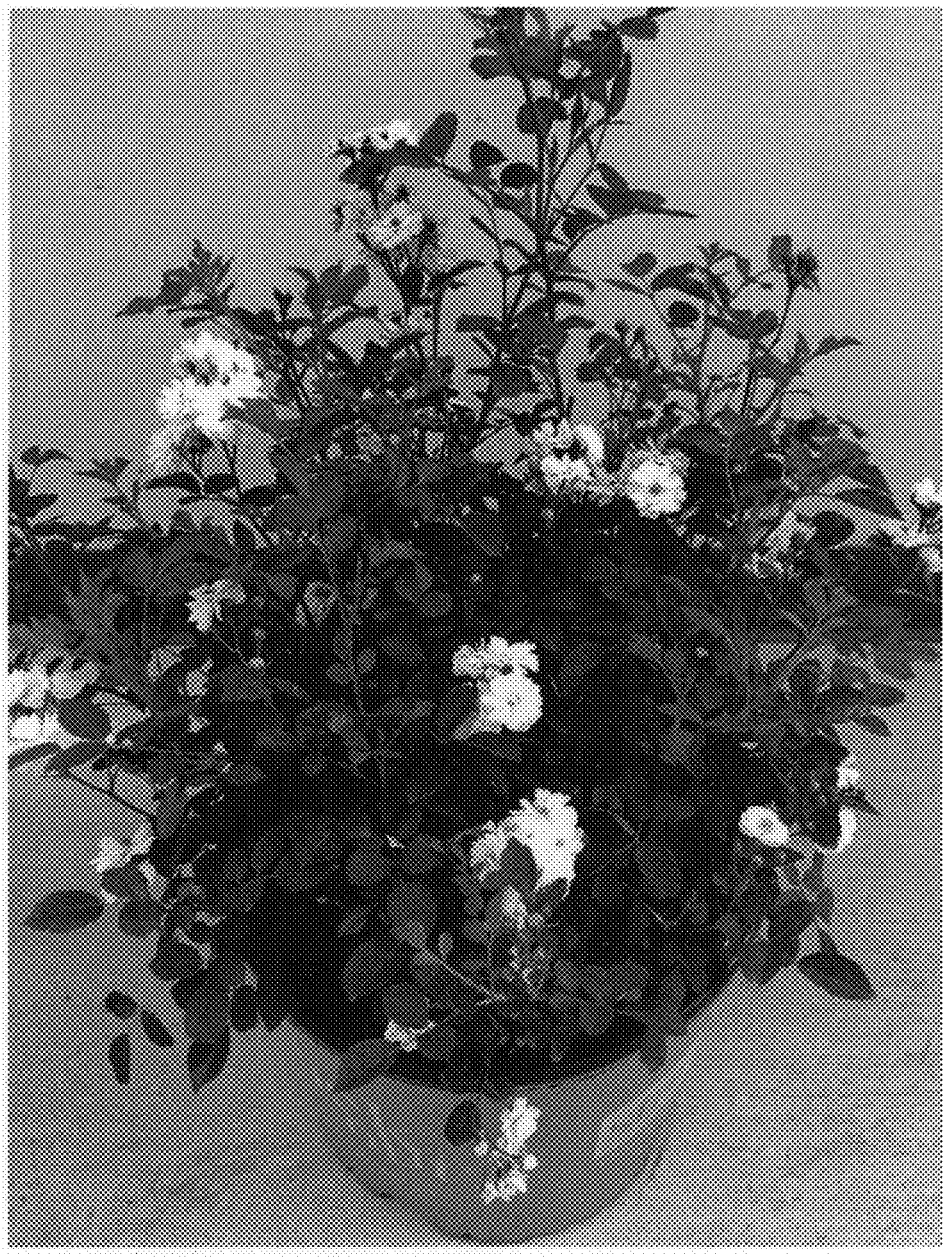

* * * * *